United States Patent [19]

Lescrenier et al.

[11] Patent Number: 4,618,980

[45] Date of Patent: Oct. 21, 1986

[54] EXIT BEAM INDICATOR FOR RADIOGRAPHIC EQUIPMENT

[75] Inventors: Charles Lescrenier, 660 Crescent Dr., Wauwatosa, Wis. 53213; Val Bautista, Spring Grove, Ill.

[73] Assignee: Charles Lescrenier, Wauwatosa, Wis.

[21] Appl. No.: 650,306

[22] Filed: Sep. 12, 1984

[51] Int. Cl.$^4$ .............................................. A61B 6/08
[52] U.S. Cl. .................................... 378/206; 378/205
[58] Field of Search ............... 378/147, 150, 151, 205, 378/206, 207, 166

[56] References Cited

U.S. PATENT DOCUMENTS 3,473,024  10/1969  Feiertag ............................... 378/209
4,167,675   9/1979  Stödberg et al. .................... 378/206
4,337,502   6/1982  Lescrenier ........................... 378/206

Primary Examiner—Craig E. Church
Assistant Examiner—Charles F. Wieland
Attorney, Agent, or Firm—Andrus, Sceales, Starke & Sawall

[57] ABSTRACT

An indicator for indicating a dimension of an X-ray beam defined by a collimator has a base member positioned on the other side of the patient from the X-ray beam source. A pair of light sources are mounted on the base member for linear movement and for angular movement so that the beams of light may be positioned into congruency with the edges of the X-ray field defined by the collimator and converge at the source of the X-ray beam. The light sources may be moved by a cable having selectively movable segments to which the light sources are attached or by lead screws.

13 Claims, 6 Drawing Figures

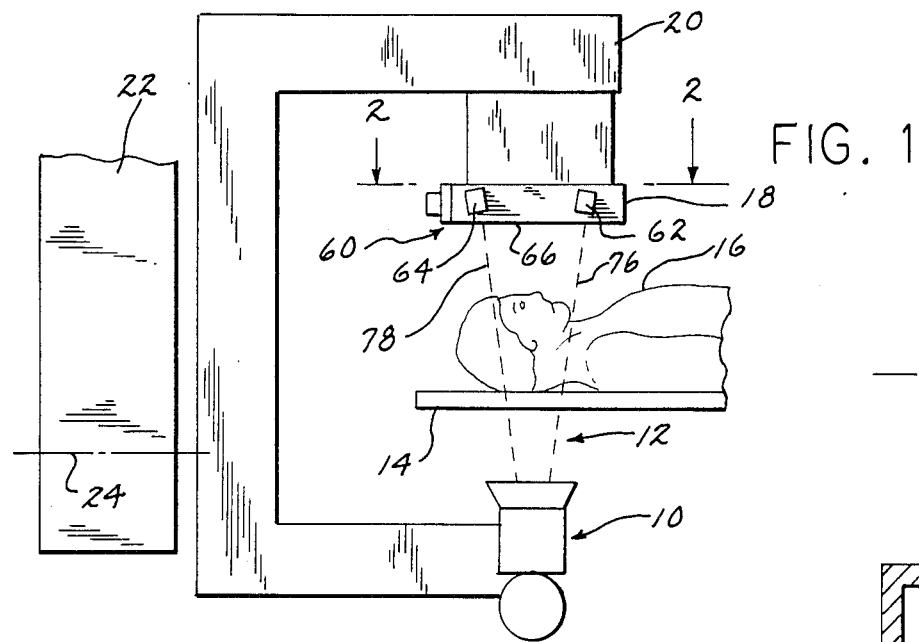
FIG. 1
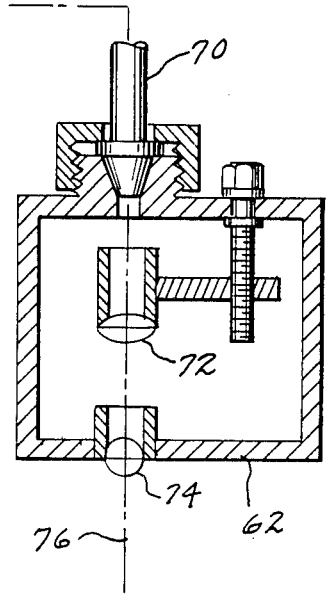
FIG. 4
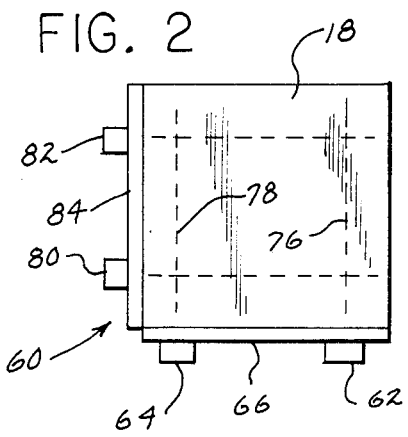
FIG. 2
FIG. 6
FIG. 5
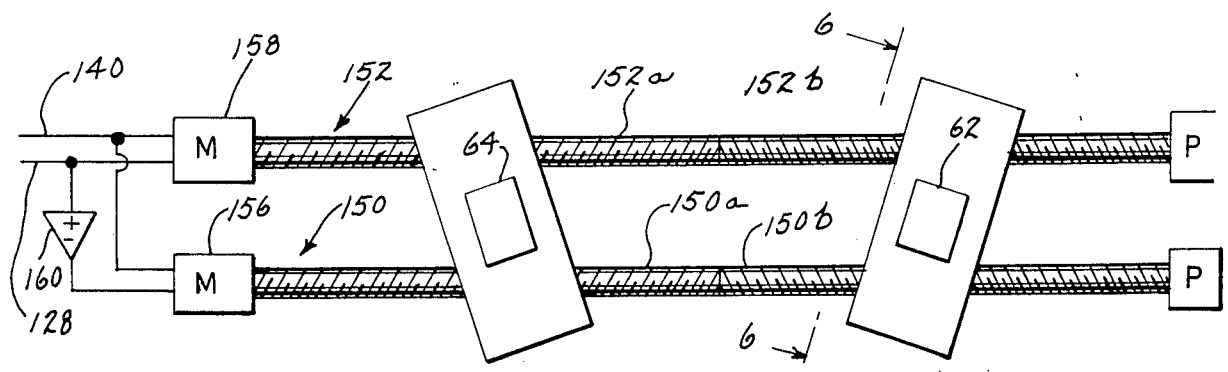

EXIT BEAM INDICATOR FOR RADIOGRAPHIC EQUIPMENT

Radiographic equipments, such as diagnostic X-ray systems, employ a collimator to determine the shape of the X-ray beam. The collimator has movable plates of radiation absorbing material, such as lead. In a typical collimator lead plates are moved toward and away from each other. Two pairs of such plates are provided that move along orthogonal axes. The X-ray generator applies the X-ray beam to one side of the patient. The X-ray beam passes through the patient onto a receptor on the other side of the patient. The receptor typically comprises a film or a fluoroscopic image intensifier.

Since X-ray radiation is invisible to the human eye, the collimator includes a visible light system that illuminates the area of the patient being exposed to radiation. Typically, the light shows through the collimator so that as the collimator plates move to establish the dimensions of the X-ray beam, the dimension of the illuminated area on the body of the patient correspondingly changes. The operator is thus appraised of the location and extent of the area being irradiated.

However, some radiographic systems are arranged so that the operator cannot see the portion of the patient where the X-ray beam enters and thus cannot be certain of the dimensions of the X-ray beam and its location with respect to the patient. This may occur in remotely controlled X-ray generator where the X-ray system is under the table on which the patient lies and the film cassette or image intensifier tube is located above the patient. The same is true in "C" or "U" arm systems where, similarly, the X-ray generator is under the table and the receptor is over the table. Because the aforesaid uncertainty, it is often necessary to make numerous X-ray exposures with various sized beams and various relative positions between the beam and the patient in order to obtain a radiograph of the desired portion of the patient. However, this subjects the patient to multiple radiation dosages which is undesirable from a medical standpoint.

One method for determining the size of the X-ray field and its location with respect to the patient is to operate the X-ray system in the fluoroscopic mode and simply look at the images on the image intensifier tube to make the necessary adjustments to the X-ray beam and the position of the patient. This method works well but, again, at the expense of undesirable exposure of the patient to radiation.

Radiation dosage to the patient may be reduced by using a light pointer providing a narrow beam that marks the center of the field of irradiation. Typically, a small surgical light is attached to the X-ray receptor. The mechanical elements of the X-ray system maintain the light in a reasonably accurate positional relationship to the exit radiation beam. The operator may thus ascertain the position of the certain of the exit beam and thus the general location of the entire beam.

However, such an arrangement does not compensate for parallax effects and does not indicate the size of the field. Each radiograph must be preceded with a short period of fluoroscopy to be certain that the area of interest will be seen in the film or image intensifier.

In some radiographic systems, no fluroscopic mode exists so that repeated exposures often must be made to insure that at least one of them contains the area of interest. As noted above, this increases the radiation dosage to the patient.

It is, therefore, the object of the present invention to provide an improved means for accurately determining the configuration and location of an X-ray beam exiting a patient. High quality radiographs of desired anatomical portions of the patient can be quickly, easily, and accurately obtained while minimizing radiation dosage to the patient. The invention is particularly suited for use in X-ray systems in which it is difficult or impossible to see the entering X-ray beam.

The present invention achieves the aforesaid and other objects by providing an outline of the area of the exiting beam that is visible to the operator of the X-ray system. The visual outline is sufficiently bright to be seen under commonly encountered ambient lighting conditions including, for example, surgical lights in an operating room.

The present invention incorporates a plurality of light sources applying planes of laser light to the side of the patient from which the X-ray beam exits. The light sources may typically be mounted on the receptor for the X-ray beam. One pair of sources is provided for each dimension of the X-ray beam to be visibly defined. The light sources move linearly toward and away from each other normal to the axis of the X-ray beam and rotate about an axis normal to the direction of linear movement and the axis of the X-ray beam. The light sources are controlled responsive to the position of the collimator plates so that the planes of light are congruent with the edges of the X-ray beam, including the exit portions thereof, and converge at the source of the beam. In this way, the patterns of light formed by the light source on the patient provide a visual indication of the dimension of the exit X-ray beam.

The light source may be moved by a cable means having a plurality of movable segments across which the light sources are attached. By selectively moving the various cable segments the light sources may be correspondingly linearly or angularly moved. Or the light sources may be moved by a lead screw mechanism.

The invention will be further understood by the following detailed description and the accompanying drawings. The drawings show as follows.

FIG. 1 is a diagrammatic view of portions of a X-ray system and the exit beam indicator of the present invention.

FIG. 2 is a view taken along the line 2—2 of FIG. 1.

FIG. 4 is a detailed cross sectional view of a light source suitable for use in the exit beam indicator of the present invention.

FIG. 5 is a somewhat schematic diagram of portions of another embodiment of the exit beam indicator of the present invention.

FIG. 6 is a partial view taken along the line 6—6 of FIG. 5.

Figure 3:
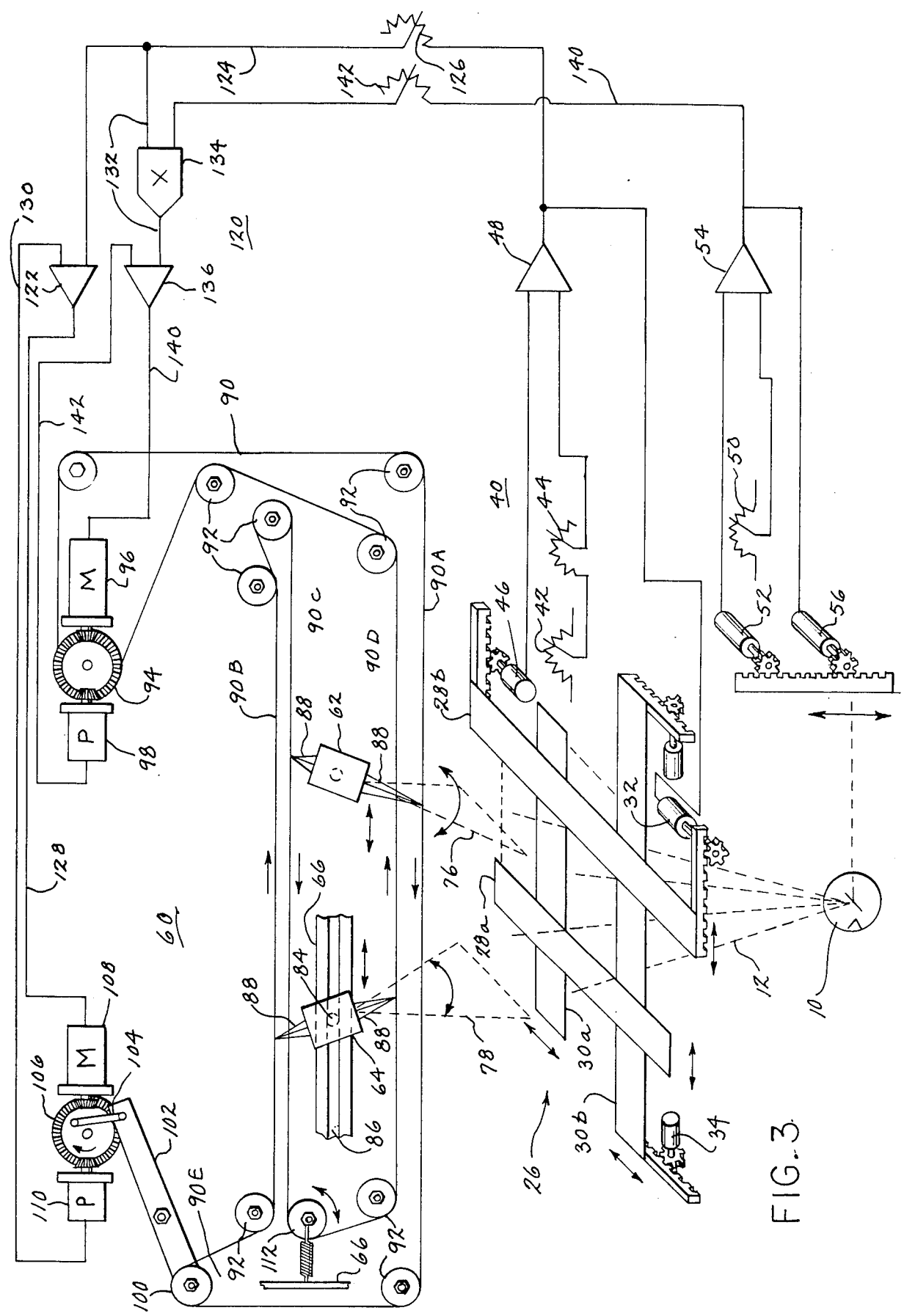
FIG. 3 is a somewhat diagrammatic view of the exit beam indicator of the present invention and associated portions of the X-ray system.

FIG. 1 shows X-ray source 10, such as an X-ray tube, emitting X-ray beam 12. X-ray source 10 is positioned below table 14 that receives patient 16. Table 14 has a removable panel or X-ray transparent portion that permits X-ray beam 12 to be applied to patient 16.

Receptor 18 for the X-ray system is positioned above patient 16 and may comprise a cassette containing X-ray sensitive film and/or a fluoroscopic image receptor tube. X-ray source 10 and receptor 18 may be mounted on a C-shaped frame 20 that is pivotally coupled to base member 22 so as to permit frame 20, X-ray source 10 and receptor 18 to rotate about a horizontal axis 24.

The shape of X-ray beam 12 is determined by collimator 26, or shown in FIG. 3. Collimator 26 a shutter including lead plates 28a and 28b. Lead plates 28a and 28b move toward each other to narrow beam 12 and away from each other to widen beam 12. Plates 30a and 30b move toward and away from each other normal to the direction of movement of plates 28a and 28b. Plates 28 and 30 define an X-ray beam of square or rectangular configuration, the dimensions of which are determined by the positions of plates 28a and 28b and 30a and 30b.

Actuators, such as electric motors 32 ad 34 may be employed to move plates 28 and 30. One actuator may be coupled to each of the plates. Or one actuator may be coupled to each pair of plates and the plates connected together by a linkage that provides the appropriate motion to the plates. Actuators 32 and 34 are controlled by a control system, hereinafter described in detail.

X-ray source 10 and collimator 26 are movable toward and away from patient 16, as shown in FIG. 3, to control the degree of X-ray magnification provided to the image received in receptor 28, i.e. the closer X-ray source 10 is to patient 16, the greater the magnification.

In the following, the control system for collimator plates 28a and 28b is described in detail. It will be appreciated that a similar control system is provided for collimator plates 30a and 30b.

Control system 40 for collimator 26 includes a reference signal source 42 for providing a signal through trimmer potentiometer 44 indicative of the desired position of the collimator plates. A signal means, such as a potentiometer 46, provides a signal indicative of the actual position of plates 28. Reference signal source 42 and feedback potentiometer 46 are connected to control amplifier 48, the output of which operates motor 32 to move plates 28 and establish one dimension of X-ray beam 12.

Reference signal source 50 provides a signal corresponding to the desired position of X-ray source 10 with respect to patient 16. Feedback potentiometer 52 provides a signal indicative of the actual position of X-ray source 10. Reference signal source 50 and feedback potentiometer 52 are connected to control amplifier 54, the output of which operates motor 56 to move X-ray source 10.

Exit beam indicator 60 of the present invention is positioned above patient 16. It may preferably be mounted on receptor 18, as shown in FIG. 1.

Also as shown in FIG. 1, exit beam indicator 60 includes a pair of light sources 62 and 64 movably mounted on bar 66 for movement with respect thereto. Specifically, light sources 62 and 64 may be translated or linearly moved toward and away from each other along bar 66 and rotated about horizontal axes normal to the bar 66.

As shown in FIG. 4, each light source 62 and 64 may comprise the exit end of a optical fiber cable 70. After passing through appropriate optics 72, the light from optical fiber cable 70 is passed through a cylindrical lens 74 to generate a plane of light 76, normal to the plane of the paper in FIG. 4 and shown in perspective in FIG. 3.

The input end of optical fiber cable 70 may be connected to a light source such as in incandescent lamp or, preferably, a laser. The latter may provide a light plane of sufficient intensity for use where high levels of ambient illumination surround the radiographic equipment, as in surgical operating rooms.

Light sources of the type described above are shown in U.S. Pat. No. 4,337,502.

The light plane 76, and the corresponding plane 78 from light source 64 provide definition to two edges of the exit X-ray beam, for example, the right and left edges of the beam, as shown in FIG. 3. This defines one dimension of the exit X-ray beam, for example, the width. As shown most clearly in FIG. 2, a second pair of similar light source 80 and 82 provide definition to the remaining edges of the exit X-ray beam. Light sources 80 and 82 are mounted on bar 84. Bar 66 may lie on one side of receptor 18 while bar 84 lies on another side of receptor 18 so as to position bar 84 normal to bar 66. All four edges, and both dimensions, of the exit X-ray beam will be defined by the two pairs of light sources 62 and 64 and 80 and 82.

As generally shown in FIG. 3, in connection with light sources 62 and 64, as collimator plates 28 are moved toward and away from each other, the light sources are correspondingly moved along bar 66 and rotated so that the light planes 76 and 78 from light sources 62 and 64 lie on the extension of the X-ray beam 12 formed by collimator 26 and converge at the source of the X-ray, such as tube 10. The lines of light formed on patient 16 when light planes 76 and 78 strike patient 16 define one dimension of the X-ray beam 12 exiting the patient. The movement of light sources 62 and 64 may be accomplished by the apparatus shown in FIG. 3.

Light sources 62 and 64 each have a pin 84 extending through an elongated slot 86 in bar 66. Pin 84-slot 86 permits light source 62 and 64 to move along the bar and rotate with respect to the bar. Arms 88 extend from either end of light sources 62 and 64. Arms 88 are connected to cable 90 extending around a series of pulleys 92 mounted on bar 66 in the manner shown in FIG. 3. Cable 90 is connected to drum 94 rotated through bevel gears by motor 96. Potentiometer 98 provides a feedback signal indicative of the position of drum 94.

Cable 90 has horizontal portions 90A, 90B, 90C, and 90D. When cable 90 is moved by the rotation of drum 94, portions 90A and 90C move in a similar direction and portions 90B and 90D move in a similar direction but opposite to portions 90A and 90C. For example, when cable drum 94 is rotated clockwise, portions 90A and 90C move to the left as shown in FIG. 3 and portions 90B and 90D move to the right.

Pulley 100 is mounted to one end of lever arm 102 pivotally mounted on bar 66. The other end of arm 102 is fastened to link 104 of disc 106. Disc 106 is rotated by motor 108 through bevel gearing. Potentiometer 110 provides a feedback signal indicative of the position of disc 106. Pulley 112 is a spring-loaded idler pulley. When disc 106 is rotated, pulley 106 and loop 90E are raised or lowered depending on the direction of rotation. This causes cable portions 90A and 90B to move in a similar direction and cable portions 90C and 90D to move in the same direction but opposite to that of sections 90A and 90B. Spring loaded idler pulley 112 accommodates the raising and lowering of loop 90E. For example, if disc 106 is rotated in the clockwise direction as shown in FIG. 3, loop 90E is raised. This causes cable sections 90A and 90B to move to the left when viewed as in FIG. 4 and cable sections 90C and 90D to move to the right. The above described operation is reversed when disc 106 is rotated counterclockwise by motor 108.

As shown in FIG. 3, upper arm 88 of light source 62 is coupled to cable section 90C. Lower arm 88 of light source 62 is coupled to cable section 90A. The upper arm 88 of light source 64 is coupled to cable section 90B. The lower arm of light source 64 is coupled to cable section 90D.

As a result of the above connection of arms 88 to cable sections 90A, 90B, 90C, and 90D, when drum 94 rotates in the clockwise direction, light sources 62 and 64 are moved toward each other. When drum 94 rotates in the counterclockwise direction, light sources 62 and 64 move away from each other. When disc 106 rotates in the clockwise direction, light source 62 rotates in the clockwise direction and light source 64 rotates in the counterclockwise direction. When disc 106 rotates in the counterclockwise direction, light source 62 rotates in the counterclockwise direction and light source 64 rotates in the clockwise direction.

Thus, by appropriate control of motors 96 and 108, light sources 62 and 64 can be translated along bar 64 and rotated with respect to it to position the light sources on bar 66 so that the light planes 76, 78 from light sources 62 and 64 form extensions of the edges of X-ray beam 12, as defined by collimator 26, and converge at X-ray tube 10, as shown in FIGS. 1 and 3. The lines of light formed on patient 16 from the planes of light of the light sources define the extent and location of the X-ray beam 12 exiting patient 16.

To provide this operation, control system 40 for collimator 26 is connected to motors 96 and 108 through control circuitry 120.

As shown in FIG. 3, the output signal of amplifier 48 is provided to amplifier 122 through conductor 124 containing trimming potemtiometer 126. The output of amplifier 122 is connected to motor 108 by conductor 128. A feedback signal is provided in conductor 130 to amplifier 122 from potentiometer 110.

The output of amplifier 48 is also provided, through conductor 132 and multiplier 134 to the input of amplifier 136. The output of amplifier 136 is connected to motor 96 by conductor 140. A feedback signal is provided in conductor 142 to amplifier 136 from potentiometer 98.

Through the above connection of collimator control system 40 to exit beam indicator control circuitry 120, as collimator plates 28 are moved by control system 20, light sources 62 and 64 are correspondingly linearly moved and rotated so that light sources 62 and 64 are congruent with the edges of X-ray beam 12 and converge at X-ray source 10. When applied to patient 16, light planes 76 and 78 will indicate one dimension of the exiting X-ray beam.

Thus, if collimator plates 28a and 28b are moved apart, light sources 62 and 64 are also moved apart. Light source 62 is rotated in the clockwise direction and light source 64 is rotated in the counterclockwise direction. This maintains the desired congruency and convergence of light planes 76 and 78. If collimator plates 28a and 28b are moved together, the reverse occurs.

As X-ray source 10 and collimator 26 is raised or lowered by motor 56 with respect to patient 16, without changing the position of collimator plates 28, the linear position of light sources 62 and 64 must correspondingly change but the rotary position of the light sources remains the same. Thus, if X-ray source 10 is lowered, light sources 62 and 64 must be moved further apart, the vice versa. For this purpose the output signal of control amplifier 54 is provided in conductor 140 through trimming potentiometer 142 to the input of multipler 134 to ratio the input signal to amplifier 136. If the position of X-ray source 10 and collimator 26 changes, the input signal to amplifier 136 will change to alter the linear position of light sources 62 and 64. Multiplier 134 may be of the semiconductor type.

The construction and operation of light sources 80 and 82 and associated apparatus defining the other dimension of the exit X-ray beam established by collimater plates 30 corresponds to those for light sources 62 and 64, described in detail above.

While an analog type system has been shown in FIG. 3, it will be appreciated that a digital system may be utilized, if desired. The feedback potentiometer would comprise digital shaft encoders and the motors would comprise stepper motors driven by pulse generators. The amplifiers would comprise microprocessors having look-up tables correlating collimator plate position and light source linear and rotary position.

It will be appreciated that the trigonometric function between the linear movement of light sources 62 and 64 and the angular movement of the light sources is slightly non-linear. Normally no significant loss inaccuracy is encountered over the typical range of arcuate movement of the light sources. However, a microprocessor may conveniently incorporate a function generator or other technique that can generate the nonlinear relationship thereby to provide very high resolution to exit beam indicator 60.

While the invention has been described above as using cable 80 to obtain the desired movement of light sources 62 and 64, it will be appreciated that other means may be employed for this purpose. FIGS. 5 and 6 shows an embodiment of the invention in which lead screws 150 and 152 are used to move light sources 62 and 64. Lead screws 150 and 152 have oppositely threaded end portions 150a and 150b and 152a and 152b, respectively. Nuts 154 threaded on lead screws 150 and 152 are mounted on light sources 62 and 64, as shown in FIG. 6 in connection with light source 62.

Motor 156 drives lead screw 150 and motor 158 drives lead screw 152. When motors 156 and 158 drive lead screws 150 and 152 in the same direction, linear movement of light sources 62 and 64 is obtained. When motors 156 and 158 drive lead screws 150 and 152 in the opposite direction, rotary movement of light sources 62 and 64 is obtained. Output conductors 128 and 140 from amplifiers 122 and 136 are connected to motors 156 and 158. Inverting amplifier 160 provides the desired differential operation of motors 156 and 158 responsive to output signals from amplifier 122.

It will be appreciated that the desired operation of lead screws 150 and 152 may be obtained by mechanical gearing, if desired.

Various modes of carrying out the invention are contemplated as being within the scope of the following claims particularly pointing out and distinctly claiming the subject matter which is regarded as the invention.

We claim:

1. An indicator for indicating at least one dimension of a X-ray beam diverging from an X-ray source, said X-ray source being located on one side of an object and the X-ray beam exiting on a second side of the object, the X-ray beam being defined by movable collimator means and having an axis, said indicator comprising:

a base member positioned on the second side of the object;

a pair of light sources mounted on said base member for generally linear movement toward and away from each other normal to the axis of the X-ray beam and for angular movement about an axis normal to the direction of linear movement of the light sources and the axis of the X-ray beam, said light sources providing beams of light for application to the second side of the object and capable of defining one dimension of said X-ray beam;

operating means for providing linear and angular movement of the light sources; and control means connected to said operating means and couplable to the collimator means for causing said operating means to move said light sources so that the beams of light are congruent with the edges of the X-ray field, as defined by the collimator means, and converge at the source of the X-ray beam.

2. An indicator according to claim 1 wherein said beams of light are planes of light forming generally parallel lines when applied to the object.

3. An indicator according to claim 1 further including a second pair of light sources, operating means, and control means mounted on said base member for defining a second dimension of the X-ray beam.

4. An indicator according to claim 1 wherein the X-ray source is movable toward and away from the object and wherein said control means includes means for altering the linear movement of said light sources in accordance with the movement of the X-ray source.

5. An indicator according to claim 1 wherein said operating means comprises cable means mounted on said base member and having a plurality of generally parallel segments, and means for moving selected ones of said segments in similar or opposite directions responsive to said control means, said light sources being coupled to said segments for obtaining said linear and angular movement from the movement of said selected ones of said segments.

6. An indicator according to claim 5 wherein said cable means includes first, second, third, and fourth segments, one of said light sources being connected between said first and third segments, the other of said light sources being connected between said second and fourth segments and wherein said cable segment moving means includes first means coupled to said control means for moving said first and third segments in the same direction and said second and fourth segments in the same direction but opposite to the direction of movement of said first and third segments to obtain said linear movement of said light sources toward and away from each other, said cable segment moving means further including second means coupled to said control means for moving said first and second cable segments in the same direction and said third and fourth cable segments in the same direction but opposite the direction of said first and second segments for obtaining angular movement of said light sources.

7. The indicator according to claim 6 wherein said first moving means comprises a drum around which said cable is wrapped.

8. The indicator according to claim 6 wherein said second moving means comprises means forming a bight in said cable and for expanding and contracting said bight to provide the angular movement of said light sources.

9. An indicator according to claim 1 wherein said operating means comprises lead screw means coupled to said light sources and motor means coupled to said lead screw means for rotating same for obtaining linear and angular movement of said light sources.

10. An indicator according to claim 1 wherein said control means is further defined as an analog control means.

11. An indicator according to claim 1 wherein said control means is further defined as a digital control means.

12. An indicator according to claim 1 wherein said light sources are further defined as providing beams of laser light.

13. An indicator according to claim 1 further defined as an indicator for the X-ray beam exiting a patient.

* * * * *